United States Patent [19]

Marschner et al.

[11] Patent Number: 4,526,780
[45] Date of Patent: Jul. 2, 1985

[54] ANHYDROUS ANTIPERSPIRANT COMPOSITION

[75] Inventors: Frank W. Marschner, Whitehouse Station; Divaker B. Kenkare, South Plainfield; James H. Bowers, Somerville, all of N.J.

[73] Assignee: Colgate-Palmolive Company, New York, N.Y.

[21] Appl. No.: 473,163

[22] Filed: Apr. 25, 1983

Related U.S. Application Data

[63] Continuation of Ser. No. 241,893, Mar. 9, 1981, abandoned.

[51] Int. Cl.$^3$ .......................... A61K 7/32; A61K 7/34; A61K 7/38
[52] U.S. Cl. .......................................... 424/66; 424/65; 424/68; 514/770; 514/772
[58] Field of Search ............................ 424/66, 65, 68

[56] References Cited

U.S. PATENT DOCUMENTS

| | | | |
|---|---|---|---|
| 4,025,615 | 5/1977 | Rubino | 424/68 |
| 4,053,581 | 10/1977 | Pader et al. | 424/66 |
| 4,065,564 | 12/1977 | Miles, Jr. et al. | 424/66 |
| 4,126,679 | 11/1978 | Davy et al. | 424/65 |

FOREIGN PATENT DOCUMENTS

| | | | |
|---|---|---|---|
| 1100882 | 3/1961 | Fed. Rep. of Germany | 424/358 |
| 795222 | 5/1958 | United Kingdom | 424/68 |
| 2013085 | 8/1979 | United Kingdom | 424/66 |

OTHER PUBLICATIONS

Ash Formulary of Cosmetic Preparations, 1977, pp. 1 to 14.

*Primary Examiner*—Dale R. Ore
*Attorney, Agent, or Firm*—Herbert S. Sylvester; Murray M. Grill; Norman Blumenkopf

[57] ABSTRACT

A novel stable anhydrous paste or cream composition having superior ultradry characteristics when applied to the skin comprising an antiperspirant or deodorant agent and an oil absorbent material homogeneously dispersed in a vehicle comprising about 25-55% of a volatile silicone and a clay suspending/thickening agent in the form of a gel, preferably a bentonite gel. Additionally preferable ingredients are stability agents to prevent syneresis (oil separation) such as the fatty acid metal salts, more specifically zinc, aluminum, calcium, magnesium, and lithium stearates. Additional thickeners, binders, suspending agents, emollients and nonionic emulsifiers may be added as desired to further enhance the aesthetics of the cream product. The resultant dryfeel cream products spread easily, are not wet, oily or sticky, and vanish almost immediately on rub-in when applied to the skin.

10 Claims, No Drawings

ANHYDROUS ANTIPERSPIRANT COMPOSITION

This is a continuation of application Ser. No. 06/241,893 filed Mar. 9, 1981, now abandoned.

The present invention relates to dry, stable, essentially anhydrous antiperspirant/deodorant creams comprising a volatile silicone vehicle, a clay suspending/thickening agent in the form of a gel, and an oil absorbent material as the essential ingredients.

BACKGROUND AND PRIOR ART

Slurries, pastes and creams are traditionally prepared as oil-in-water or water-in-oil emulsions. Antiperspirants prepared with these emulsions go on the skin either wet or oily and are often sticky. They also require time to dry. Oil based liquid roll-ons on the other hand require shaking. They go on oily and also require time to dry.

Anhydrous antiperspirant compositions are known in the prior art and are described in U.S. Pat. No. 3,873,686 wherein a liquid formulation, which may also be in the form of a cream and is preferably in the form of an aerosol, comprises an alcohol soluble aluminum chlorhydroxidepolyol complex antiperspirant in an anhydrous ethanol vehicle; and in stick form as disclosed in U.S. Pat. No. 4,137,306. Anhydrous liquid compositions having particular utility in pump-spray or roll-on formulations, wherein the antiperspirant agents are dissolved in a vehicle containing ethanol and a sufficient amount of volatile and/or non-volatile silicone liquids to reduce tackiness of the antiperspirant, is described in U.S. Pat. Nos. 4,053,581, 4,065,564 and 4,073,880. In an attempt to improve the drying properties of antiperspirant compositions, the Product Bulletin of Wickhen Products, Incorporated, received May 24, 1979, describes a roll-on suspension containing an antiperspirant agent in a vehicle comprising 69–77% volatile silicone, 2% ethanol and 1% water.

U.K. Patent Application GB No. 2018590A eliminates the alcohol content from the roll-on or pump-spray antiperspirant suspension vehicle and substitutes a volatile cyclic silicone in amounts of 60–95% in order to improve adherence of said antiperspirant to the axillae, thereby improving efficacy. Despite the inclusion of suspending agents in the above formulation, some shaking is necessary in order to redisperse settled antiperspirant.

British Pat. Nos. 1,485,373, 1,501,862 and 2,003,730 disclose a moisture-absorbent water-insoluble and/or water-soluble polymer, (i.e., starch) as a substitute for astringent antiperspirant compounds, in an alcohol vehicle, said formulations being in the form of roll-on lotions, spray-pump liquids or aerosol sprays.

Another attempt to avoid greasy and tacky antiperspirant products resulted in solid stick formulations containing antiperspirant powder (i.e., aluminum salts) suspended in a solid vehicle comprising volatile silicones and long chain alcohols which may contain other powdered materials such as talc, starch, clays, sodium bicarbonate and fumed silica, as disclosed in U.S. Pat. No. 4,126,679.

Although antiperspirant cream formulations are commonly manufactured as oil in water emulsions, anhydrous creams in the form of a thixotropic gel is disclosed in U.S. Pat. No. 4,083,956, wherein a powdered astringent material is suspended in a liquid emollient such as mineral oils, or fatty acid and fatty alcohol esters containing an inorganic clay thickening/suspending agent, and a gel promoting agent such as $C_{1-5}$ alkanols or propylene carbonate. This cream is in the form of a gelled mixture.

Despite the many attempts to provide a dry cream product, there is no disclosure of an anhydrous paste or cream composition which is stable, i.e., resistant to syneresis and requires no shaking prior to use, is easily spreadable, is not wet, oily, sticky or greasy and vanishes almost instantly on rub-in, requiring essentially no drying time, comprising an antiperspirant agent, an oil absorbent material, in a volatile non-polar vehicle such as volatile silicone and a clay suspending/thickening agent in the form of a bentonite gel.

SUMMARY OF THE INVENTION

The primary object of the invention is to overcome existing disadvantages and difficulties by providing a novel stable antiperspirant, deodorant cream or paste product which requires no shaking prior to use.

Another object of this invention is to provide an anhydrous cream or paste product which requires essentially no drying time when applied to the skin.

Still another object of this invention is to provide a dry feel cream or paste with improved aesthetics, i.e., is not wet, oily or sticky upon application to the skin.

Another object of this invention is to provide a product capable of being readily and easily applied to the skin by simply spreading with a pad or fingers.

Still another object of instant invention is to provide an efficacious antiperspirant/deodorant cream or paste formulation cosmetically acceptable for sale as consumer products.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects and in accordance with the present invention, as embodied and broadly described herein, the antiperspirant/deodorant product of this invention comprises a stable, dry-feel anhydrous cream comprising an antiperspirant and/or deodorant agent and an oil absorbent material dispersed in a volatile silicone vehicle containing a clay suspending thickening agent in the form of a bentonite gel.

More specifically, present invention relates to stable, quick vanishing/drying anhydrous antiperspirant/deodorant compositions in the form of a cream or paste which is dry upon application to the skin and requires no shaking prior to use, and substantially no drying time, containing as the essential ingredients about 25–55% of a volatile silicone vehicle; at least 10% and up to 50% and preferably 15–30% by weight of an oil absorbent material selected from the group consisting of talc, starches, clay, microcrystalline cellulose and grain derived products and mixtures thereof; about 10–30% antiperspirant and/or deodorant agent; and about 1.0–20% by weight of a clay suspending/thickening agent which is in the form of a gel; and preferably about 0.1–6% by weight of a stearate salt.

It has been found that superior antiperspirant/deodorant products can be formulated as pastes, or creams which require no shaking and require essentially no drying time. Furthermore, they vanish almost immediately on rub-in and have superior ultra dry characteristics without imparting an oily or greasy after-feed to the skin. The user, therefore, can dress almost immediately after applying the product. These products are essentially anhydrous and contain volatile non-polar vehicles in combination with oil absorbent materials. Less oils are used, which when combined with oil absorbent materials make for unique ultradry type antiperspirant/deodorant products. Thickeners, binders and suspending agents are useful in the formulations to improve product aesthetics and product stability. O/W emulsifiers are also useful to improve the rinseability of the products from the skin.

Accordingly, an anhydrous antiperspirant/deodorant cream comprising an antiperspirant and/or deodorant agent dispersed in the volatile silicone vehicle containing a clay suspending/thickening agent and at least one oil absorbent material offers many advantages and are unexpectedly superior to water-based antiperspirant/deodorant emulsions, and superior to oil-based liquid roll-on antiperspirants and deodorants, as evidenced by the nature of the instant novel products which are ultradry, not wet, oily or sticky and require essentially no drying time. In addition, instant novel creams are stable, i.e., no settling out of antiperspirant or deodorant agent, have a good shelf life, free of syneresis, and require essentially no shaking prior to use. Instant novel creams are more spreadable and non-greasy compared to antiperspirant or deodorant sticks. Unlike liquid roll-ons, they are not runny, wet or oily, but dry in use. Instant novel anhydrous creams have eliminated the multiple disadvantages of prior art formulations and achieved an unexpectedly superior product both as to aesthetics and effectiveness.

The vehicle into which the antiperspirant and/or deodorant active ingredient is dispersed, is non-polar and is a volatile silicone. This vehicle facilitates the almost instantaneous absorption of said active ingredient into the skin; eliminates the stinging sensation attributable to ethanol which is a commonly used polar vehicle and the wet feeling of an aqueous vehicle. This volatile silicone oils may be cyclic silicones represented by the formula —$[R_2SiO]_n$— wherein R is $C_1$–$C_4$ alkyl and n is 3 to 10 preferably from 3 to 7, and the unsatisfied valencies on the oxygen and silicon atoms at the ends of the chain are joined to one another to form a cyclic structure. Suitable volatile cyclic silicones are for example, (a) U.C.C.Y-7207 sold by Union Carbide Corporation in which each R is a methyl group and which typically comprises, by weight, 99.4% tetramer, 0.6% trimer and traces of the pentamer and hexamer, (b) SWS-03314 (sold by SWS Silicones, a Division of Stauffer Chemical Company) in which R is a methyl group and which is substantially all tetramer, and (c) Dow Corning 344 fluid in which R is a methyl group and which typically comprises, by weight, about 88% tetramer, about 11.8% pentamer and traces of trimer and hexamer, and more specifically cyclomethicone, a cyclic dimethyl polysiloxane compound. The volatile silicone oil may also be linear polydimethylsiloxanes. The non-polar vehicle constitutes about 25–55% and preferable 30–45% by weight of the composition.

The oil absorbent material, an essential ingredient in instant anhydrous formulations, is a finely divided powder selected from the group consisting of talc, starches, clays, microcrystalline cellulose, grain derived powders such as rice, and mixtures thereof. This oil absorbent powder increases the density of the cream product, enhances its stability and drying properties and provides the cream with a dry-feel upon application to the skin. The oil absorbent filler makes the cream dry by absorbing the volatile silicone and functions as the drying medium in this system. The combination of the oil absorbent powder and the non-polar silicone vehicle forms a non-sticky film on the skin which has a velvety smooth dry feel. The oil absorbent particulate material constitutes at least 10% and preferably 15–30% and up to 50% by weight of the total composition.

The present cream formulations essentially contain an antiperspirant and/or a deodorant active material in powdered form. Any aluminum or zirconium astringent antiperspirant salt or complex, well known in the art can be employed, such as zirconyl hydroxy halides, basic aluminum halides, zirconium aluminum glycine complex, aluminum chlorides, a blend of aluminum chlorohydrate, aluminum chloride and urea, aluminum chlorhydroxide-propylene glycol complex (Rehydrol from Reheis Chemical Co.), mixtures thereof and the like. Any known deodorant active agent such as sodium bicarbonate, zinc ricinoleate may also be utilized per se or in conjunction with the antiperspirant active component where compatible. The amount of active agent used should be sufficient to provide sweat reduction and/or deodorant properties to the composition and may vary over a wide range. However, amounts of at least 5% and preferably 20 to 30% are preferred.

Another essential ingredient of the present anhydrous cream antiperspirant product is about 1.0–20% by weight of a clay suspending/thickening agent in the form of a gel, containing about 0.1–10% clay, gelled in a non-polar vehicle selected from the group consisting of volatile silicone, fatty esters (isopropyl myristate), volatile hydrocarbon, fatty alcohols (isocetyl alcohol), ethoxylated and propoxylated fatty alcohols. This clay gel thickens the volatile silicone vehicle, enhances product stability and prevents oil separation (syneresis). Said clay gels may be preformed in a non-polar vehicle in the presence of a wetting agent such as propylene carbonate and subjected to a high shearing action, such as an homogenizer at 5,000–6,000 psig prior to its addition to the volatile silicone vehicle; or said gel may be formed in situ in said silicone vehicle from the gel-forming ingredients (clay, non-polar vehicle and wetting agent) during the process of making the cream product. Suitable clay thickening/suspending agents include bentonite gels, hectorite gels and colloidal magnesium aluminum silicate gels and hydrophobically treated bentonite gels available under the tradename of "Bentone" which is prepared by reacting bentonite in a cation exchange system with an amine and forming a gel thereof in a non-polar vehicle such as isopropyl myristate, volatile silicone and mixtures thereof. Different amines are reacted to obtain a variety of Bentones which may also differ in proportions of $SiO_2$, MgO and $Al_2O_3$. Specific examples within the scope of the present invention are Bentone 38, Bentone 34, Bentone 27, and Bentone 14, all of which have a particle size below about 5 microns and are commercially available from the N L Industries, Bentone 38, a Quaternary Ammonium Hectorite clay, is the most preferred suspending/thickening agent.

Minor amounts of fumed silica (Cab-O-Sil from the Cabot Corp.) is an additionally suitable suspending agent which may be used in conjunction with aforesaid clay suspending agent. The fumed silica aids in absorbing the silicone oil and in preventing syneresis. However, the use of fumed silica as the sole thickening agent yields an unstable product wherein the oil separates out.

Minor amounts of about 0.5–10% by weight of higher fatty acid amides may be additionally used either singly or in combination as oil absorbing binding and thickening agents. Suitable amides include stearoyl monoethanolamide, cocomonoethanolamide and the like.

Nonionic emulsifiers are an optionally preferred ingredient in instant composition because it provides enhanced rinseability of the antiperspirant film from the body. Suitable nonionic emulsifying agents include alkoxylated, such as ethoxylated and propoxylated, fatty ethers and alcohols such as Polyoxyethylene (20) isohexadecyl ether, Polyoxyethylene (100) Stearyl alcohol, Polyoxypropylene (15) Stearyl ether, etc. and mixtures thereof. Amounts of 0.1–5% by weight may be used.

Another optionally preferred ingredient is a fatty acid metal salt which functions as a stability agent to prevent syneresis. Suitable metal salts include zinc, aluminum, lithium, calcium and magnesium salts of $C_{12}$–$C_{22}$ saturated and unsaturated fatty acids. Typical fatty acid salts include myristates, palmitates, stearates, etc. in amounts of 0.1–6% by weight.

In addition to the essential ingredients of the present composition, one may also include therein minor amounts of components such as perfumes, coloring agents, whitening agents such as titanium dioxide, antioxidants, ultraviolet absorbers to enhance the color and the like, so as to improve the aesthetic value and consumer acceptability. Minor amounts of other ingredients which do not adversely affect the beneficial properties of instant composition may also be included.

Minor amounts of emollients such as fatty esters, fatty alcohols, mineral oil, polyether siloxane copolymer may also be included in present novel creams to provide lubricity to the final product. Examples of emollients include isopropyl myristate, isopropyl palmitate, cetyl acetate, cetyl propionate, diisopropyl adipate, PPG-15 stearyl ether, etc. Said emollients may be solid waxes or liquid oils.

The anhydrous cream formulations of present invention are used in the same manner as any conventional antiperspirant composition to inhibit axillary perspiration. The present composition can be easily rubbed into the skin leaving a dry, non-sticky, non-oily, non-greasy, non-stinging, smooth vanishing film on the skin. The present cream compositions can be easily applied by any suitable means including the use of fingers, pads, or sheets of various substrates, brush, daubers and convenient cream dispensers known by those in the art; and can be packaged in any suitable container including jars, packets, tubes, bottles, and extruding devices, known in the prior art.

The method of making the stable anhydrous cream compositions of instant invention generally comprises mixing a clay suspending agent which is in the form of a gel with the silicone oil vehicle until a viscous solution is formed, sequentially blending and mixing the antiperspirant and/or deodorant powder and the oil absorbent particulate material with said viscous solution to form a stable cream product. More specifically, a bentonite gel, a preferred suspending/thickening agent, is formed by mixing a non-polar vehicle or combination such as isopropyl myristate and volatile silicone with Bentone and a wetting agent such as propylene carbonate and homogenizing said mixture to form a gel. Thickening of the volatile silicone can also be achieved during the batch making procedure using part or full formula amounts of the non-polar vehicle or vehicles, Bentone, wetting agent, and homogenizing the mixture, thereby forming the bentonite gel in situ and imparting thickening properties to the volatile silicone vehicle. A bentonite gel may also be purchased as a proprietary product. Said bentonite gel suspending agent and the silicone oil are mixed and heated to a temperature within the range of about 140°–220° F. until a viscous solution is formed, sequentially mixing and blending the antiperspirant powder and the oil absorbent powder with said viscous solution to form a stable viscous mixture which may be homogenized in a warm pourable state to effect a homogeneous non-pourable cream on cooling. Additional suspending agents, thickening agents, stability agents and nonionic emulsifiers may be melted and preblended with the oil absorbent powder or the antiperspirant powder prior to their addition to said viscous non-polar silicone oil vehicle, or may be preblended and added independently to said viscous vehicle or melted and added separately to said viscous vehicle. Perfume and colorants are added to the viscous mixture after cooling to between 110° and 150° F. It is preferable to homogenize the final mixture to effect a homogeneous cream product of the desired viscosity which is of a non-pourable consistency. The final product may have a non-pourable consistency at ambient temperature, a heavy cream consistency or a thick paste consistency.

DETAILED DESCRIPTION OF THE INVENTION

The following specific examples are further illustrative of the present invention, but it is understood that the invention is not limited thereto. All amounts of various ingredients are by weight unless otherwise specified.

EXAMPLE 1

| Ingredient | % |
| --- | --- |
| Bentone Gel "A" | 11.806 |
| Lithium Stearate | 0.800 |
| Antiperspirant Powder (1) | 20.000 |
| Volatile Silicone (2) | 40.394 |
| Talcum powder | 25.000 |
| Atlas G3758 (3) | 2.000 |
| Bentone Gel "A" | |
| Isopropyl Myristate | 84.706 |
| Bentone 38 (4) | 11.765 |
| Propylene Carbonate | 3.529 |

(1) Spray Dried blend of 90 parts aluminum chlorohydrate 10 parts Aluminum Chloride 5 parts Urea.
(2) Cyclomethicone a cyclic dimethyl polysiloxane compound D.C. 344 Fluid, F222 Siloxane-SWS.
(3) Polyoxyethylene (100) Stearyl alcohol - ICI.
(4) Quaternium ammonium Hectorite clay - NL Industries.

Procedure for Bentone Gel "A"

Bentone 38 is mixed with Isopropyl Myristate and Propylene Carbonate is added. The mixture is passed through a Single Stage Manton Gaulin homogenizer at 5,000–6,000 psig. A very thick non-pourable gel is obtained.

Procedure

Lithium Stearate is mixed with Bentone Gel "A" and heated hot to form a thick paste. The mixture is cooled to about 140° F. and Volatile Silicone (at 140° F.) is added and mixed to form a viscous solution. Atlas G3758 is melted and added. Talcum Powder and antiperspirant powders are blended in with mixing, and the mixture is homogenized. A viscous cream product is formed.

The above product when applied to the skin has a smooth dry feel (non-oily, non-sticky) with excellent aesthetic properties.

EXAMPLE 2

| Ingredient | % |
| --- | --- |
| Talcum powder | 25.0 |
| Bentone Gel "A" of Example 1 | 15.0 |
| Volatile Silicone of Example 1 | 32.5 |
| Cab-O-Sil (5) | 1.0 |
| Antiperspirant Powder of Example 1 | 20.0 |
| Witcamide 70 (6) | 2.0 |
| Atlas G3758 of Example 1 | 2.0 |
| Arlamol E (7) | 2.0 |
| Perfume | 0.5 |

(5) Fumed Silica - Cabot Corporation.
(6) Stearoyl Monoethamolamide - Witco.
(7) Polyoxypropylene (15) Stearyl ether - ICI Procedure The Bentone Gel is dispersed in Volatile Silicone. Cab-O-Sil is admixed followed by antiperspirant powder and talcum powder. Atlas G3758, Witcamide 70 and Arlamol E is combined, melted and mixed separately then added to the mixture. Perfume is added. A paste-type antiperspirant cream product is formed, having a light cream consistency.

The above product is dry (not oily or sticky) when applied to the skin with exceptional aesthetic properties, has a velvety smooth feel and forms a non-sticky film on the skin.

This product showed no liquid separation (syneresis) after a predetermined aging period at 110° F. and 40° F.

EXAMPLES 3 AND 4

| Examples | 3 | 4 |
| --- | --- | --- |
| Part A | | |
| Bentone Gel "A" | 15.0 | 4.0 |
| Volatile Silicone (2) | 36.0 | 42.0 |
| Part B | | |
| Antiperspirant Powder (1) | 20.0 | 20.0 |
| Arlasolve-200 (polyoxyethylene (20) isohexadecyl (ether) | 2.0 | 2.0 |
| Part C | | |
| Talc | 22.0 | — |
| Dryflo Starch (Al Starch) octenyl succinate | — | 25.0 |
| Cab-O-Sil M-5 | 1.0 | 2.0 |
| Witcamide 70 (6) | 1.0 | 1.5 |
| Cocomonoethanolamide | 2.0 | 3.0 |
| Part D | | |
| Color/Perfume | q.s | q.s |

Procedure for Examples 3 and 4

Part A is mixed and heated to 160° F. Part B ingredients are added to Part A and mixed. Part C is preblended and added to Parts A and B. The mixture is cooled to about 110° F. and perfume and color is added. The mixture is homogenized.

Examples 3 and 4 are dry (not oily or sticky) when applied to the skin with excellent aesthetic properties.

Example 4 with Dryflo Starch is white in appearance whereas 3 has a grayish color.

EXAMPLE 5

| Ingredient | % |
| --- | --- |
| Bentone Gel (from NL Industries) (made with volatile silicone and isopropyl myristate) | 15.0 |
| Volatile Silicone (SWS 03314) | 33.8 |
| Silicone Copolymer (polyether siloxane copolymer) | 3.0 |
| Aluminum/Zirconium Trichlorohydrex powder (aluminum chlorohydroxide + zirconium chlorhydroxide and glycine complex) | 20.0 |
| Italian Talc | 28.0 |
| Perfume | 0.2 |

The silicone copolymer is dissolved in hot volatile silicone and the Bentone gel is added with mixing to form a viscous solution. The aluminum-zirconium complex is admixed, followed by the talc and then the perfume and the total mixture is homogenized and cooled.

This product has a soft texture and an excellent feel when applied to the skin, and exhibits no oil separation after a predetermined aging period at 120° F.

EXAMPLE 6

| Ingredient | % |
| --- | --- |
| Bentone Gel (from NL Industries) | 5.0 |
| Volatile Silicone (SWS 03314) | 36.8 |
| Aluminum/Zirconium Trichlorohydrex powder | 20.0 |
| Perfume | 0.2 |
| Stearyl alcohol | 8.0 |
| Montana talc | 25.0 |
| Polyoxyethylene (100) Stearyl alcohol | 3.0 |
| Polyethoxylated (16.5) isohexadecyl ether (emulsifier) | 4.0 |

This composition is prepared in accordance with the procedure of Example 5.

This antiperspirant is in the form of a thick paste, has a very firm texture and good drying properties, and is stable, i.e., exhibits no syneresis after a predetermined aging period at 120° F.

EXAMPLE 7

| Ingredient | % |
| --- | --- |
| Volatile silicone (SWS 03314) | 39.5 |
| Bentone gel (NL Industries) | 8.0 |
| Zinc stearate | 2.5 |
| Montana Talc | 25.0 |
| Aluminum chlorohydrex P.G. (a propylene glycol complex) | 20.0 |
| Silicone copolymer | 5.0 |

This product is prepared in accordance with the procedure of Example 6.

This product showed no liquid separation after a predetermined aging period at 120° F.

EXAMPLE 8

Volatile silicone DC 344, which is less volatile than SWS 03314, was substituted for SWS 03314 in Example 7. The volatile silicone, bentone gel, zinc stearate and silicone copolymer were mixed at a temperature of 220° F. and cooled to 160° F. for the addition of the astringent powder and further cooled to 115° F. for the addition of the talc.

The resultant product is a thick paste with excellent stability properties.

The best stability properties are obtained using formulas containing the silicone copolymer and the aluminum chlorohydrex P.G. astringent.

EXAMPLE 9

| Ingredient | % |
| --- | --- |
| Part A | |
| Bentone gel (approx. .12%) | 4.0 |
| Volatile Silicone | 42.0 |
| Part B | |
| Talc | 20.0 |
| Antiperspirant Powder (1) | 20.0 |
| Cocomethanolamide | 6.0 |
| Stearoylmethanolamide | 6.0 |
| Polyoxyethylene (20) isohexadecyl ether | 1.5 |
| Part C | |
| Perfume | 0.5 |

Bentone gel and volatile silicone are mixed with a lightening stirrer at moderate speed and heated to 165°–170° F. The remaining ingredients of Part B are added with mixing until a viscous and homogeneous mixture is formed, which is cooled while still mixing and the perfume is added.

The color of the resultant cream is dark. Aging results at 120° F. after 4 days showed no separation, or bleeding, indicating a stable product.

EXAMPLE 10

Example 9 was repeated except that 1% TiO$_2$ was added and the Talc content was reduced to 19%, yielding a whiter product than the formulation of Example 9.

EXAMPLE 11

Example 10 was repeated except that the TiO$_2$ content was increased to 1.5%, the ethoxylated isohexadecyl ether content was increased to 2.5% and 0.5% color solution (a blue, yellow and green combination), was added and the talc and silicone content were each reduced 1% to 18% and 41% respectively.

The resultant product was a cream with good aesthetics, and exhibited good rinseability.

EXAMPLE 12

Example 4 is repeated except that 25% rice powder is substituted for the starch ingredient. The resultant product is a uniform brown mixture. It has some drag as compared to compositions containing starch or talc as the oil absorbent filler, but possesses good rub out characteristics and is stable as shown by no separation after aging for 2 weeks at room temperature and 120° F.

EXAMPLE 13

| Ingredient | % |
| --- | --- |
| Cyclomethicone (volatile silicone from SWS Silicones) | 40.6 |
| Dryflo starch (Al starch) octenyl succinate | 25.0 |
| Aluminum-Zirconium trichlorohydrex powder | 20.0 |
| Cocomethanolamide | 3.0 |
| Polyethoxy (20) iso-hexadecyl ether | 2.0 |
| Stearoylmethanolamide | 1.5 |

| Ingredient | % |
| --- | --- |
| Zinc Stearate | 1.5 |
| Bentone gel (3.4% isopropyl myristate, 0.48% Bentone 38, 0.14% propylene carbonate) | 4.0 |
| Cab-O-Sil | 2.0 |
| Perfume | 0.4 |

This product was prepared by mixing the bentone gel the silicone, the ethoxylated ether, both amide compounds and the zinc stearate while heating this mixture to 190°–220° F. until melted and a uniform viscous mixture is obtained. A mixture of the deodorant powder, the starch and the Cab-O-Sil are added to the viscous mixture at a temperature of 160°–170° F. with mixing. The perfume is admixed therewith at 160° F. and the final mixture homogenized.

This cream spreads easily and vanishes on rub-in, imparting a non-oily, non-greasy, ultradry feel to the skin. The product showed no liquid separation (syneresis) after aging 3 months at temperatures ranging between 0°–120° F.

EXAMPLE 14

Example 13 was repeated using a 50:50 blend of talc and dryflo starch in lieu of the 25% starch ingredient.

The final cream is stable and also exhibits a good, smooth, dry feel upon application to the skin.

Other volatile silicones and mixtures of volatile silicones may be substituted as the non-polar vehicle for the particular silicones in the above examples. Similarly, other oil absorbing fillers and mixtures of fillers can be substituted for the talc, dry-flo starch or rice flour in the above examples. Likewise other antiperspirant and/or deodorant powders and mixtures thereof can be substituted for the particular active agents used in the examples. Any other bentonite gel can be substituted for the specific Bentone gels utilized in the examples. Similarly, other suspending agents, stabilizing agents, thickeners, binders and nonionic emulsifiers may be substituted for the specific agents used in the examples as a means of obtaining creams of the desired consistency and aesthetic properties.

The anhydrous antiperspirant creams of present invention which comprise an antiperspirant and/or deodorant powder and an oil absorbing filler homogeneously dispersed in a volatile silicone vehicle comprising a bentonite gel as the essential suspending agent exhibit unique and superior properties such as ultradry characteristics, both as to feel and require substantially no drying time, stability upon aging as well as require no shaking prior to use, delivers a smooth coating to the skin which is readily rinseable therefrom.

It is understood that the foregoing detailed description is given merely by way of illustration and that variations may be made therein without departing from the spirit of the invention. The "Abstract" given above is merely for the convenience of technical searchers and is not to be given any weight with respect to the scope of the invention.

We claim:

1. A stable dry-feel essentially anhydrous cream composition comprising about 10–30% by weight of an antiperspirant and/or deodorant active agent and about 10–50% by weight of an oil absorbent powdered material selected from the group consisting of talc, starches, clay, microcrystalline cellulose, grain flours, and mixtures thereof, homogeneously dispersed in a nonpolar vehicle comprising about 25–55% by weight of a volatile silicone, and about 1–20% by weight of a gelatinized clay in a nonpolar vehicle as suspending/thickening agent selected from the group consisting of bentonite gels, hectorite gels, magnesium aluminum silicate gels, and hydrophobically treated bentonite gels prepared by reacting bentonite in a cation exchange system with an amine.

2. The cream according to claim 1, wherein the gelatinized clay suspending/thickening agent contains about 0.1–10% clay gelled in a nonpolar vehicle.

3. The cream according to claim 1, which additionally contains about 0.1–6% of a fatty acid metal salt selected from the group consisting of zinc, aluminum, lithium, calcium and magnesium salts of $C_{12}$–$C_{22}$ saturated and unsaturated fatty acids.

4. The anhydrous cream according to claim 1, wherein the antiperspirant agent is selected from the group consisting of aluminum and zirconium salts or complexes and mixtures thereof.

5. The cream according to claim 1, wherein the gel is a bentonite gel and the non-polar vehicle is selected from the group consisting of fatty esters, volatile silicone, volatile hydrocarbon, fatty alcohols, polyoxyethylene fatty alcohols, polyoxypropylene fatty alcohols and mixtures thereof.

6. The cream according to claim 5, which additionally contains about 0.1–5% by weight of a nonionic emulsifier selected from the group consisting of polyoxyethylene fatty ethers, polyoxyethylene fatty alcohols, polyoxypropylene fatty ethers and polyoxypropylene fatty alcohols.

7. The cream according to claim 4, wherein the antiperspirant agent is aluminum chlorohydroxide plus zirconium hydroxychloride and glycine complex, the volatile silicone is cyclomethicone, and the oil absorbent material is starch.

8. The cream according to claim 3, which additionally contains about 0.5–10% by weight of at least one higher fatty acid amide.

9. The method of preparing the anhydrous cream defined in claim 1, which comprises mixing the clay gel suspending agent with the volatile silicone oil vehicle and heating to a temperature of about 140°–220° F. until a viscous solution is formed, sequentially mixing and blending the antiperspirant/deodorant powder and the oil absorbent powder with said viscous solution to form a stable viscous warm pourable mixture, homogenizing said warm pourable mixture and cooling to form a homogeneous non-pourable cream.

10. The method according to claim 9, wherein the clay gel is formed in situ from clay, non-polar vehicle and wetting agent after homogenizing the mixture in the silicone vehicle.

* * * * *